(12) United States Patent
Geim et al.

(10) Patent No.: US 10,345,490 B2
(45) Date of Patent: Jul. 9, 2019

(54) PLASMONIC STRUCTURES AND DEVICES

(71) Applicant: The University of Manchester, Manchester (GB)

(72) Inventors: Andre Konstantin Geim, Manchester (GB); Vasyl Grigorievich Kravets, Manchester (GB); Alexander Nikolaevich Grigorenko, Manchester (GB)

(73) Assignee: The University of Manchester, Manchester (GB)

( * ) Notice: Subject to any disclaimer, the term of this patent is extended or adjusted under 35 U.S.C. 154(b) by 0 days.

(21) Appl. No.: 15/311,655

(22) PCT Filed: May 14, 2015

(86) PCT No.: PCT/GB2015/051432
§ 371 (c)(1),
(2) Date: Nov. 16, 2016

(87) PCT Pub. No.: WO2015/173580
PCT Pub. Date: Nov. 19, 2015

(65) Prior Publication Data
US 2017/0090077 A1     Mar. 30, 2017

(30) Foreign Application Priority Data

May 16, 2014 (GB) .................................. 1480727.4

(51) Int. Cl.
*G02B 5/00* (2006.01)
*G01N 21/552* (2014.01)
(Continued)

(52) U.S. Cl.
CPC ........... *G02B 5/008* (2013.01); *G01N 21/553* (2013.01); *G02B 6/1226* (2013.01); *G02B 6/132* (2013.01); *G02B 2006/12138* (2013.01)

(58) Field of Classification Search
CPC ........ G02B 6/1226; G02B 2006/12138; G02B 5/008; G02B 6/132; G01N 21/553
(Continued)

(56) References Cited

U.S. PATENT DOCUMENTS

| 2008/0272302 A1* | 11/2008 | Frey | ........................ | B82Y 20/00 250/336.2 |
| 2009/0220194 A1* | 9/2009 | Williams | ............... | B82Y 20/00 385/30 |
| 2012/0257204 A1* | 10/2012 | Walters | ................ | G01N 21/553 356/445 |

FOREIGN PATENT DOCUMENTS

| EP | 2737348 A1 | 6/2014 |
| WO | 2013186985 A1 | 12/2013 |
| WO | 2015173580 A1 | 11/2015 |

OTHER PUBLICATIONS

PCT/GB2015/051432 International Search Report and Written Opinion dated Jul. 21, 2015, 16 pages.
(Continued)

*Primary Examiner* — Tri T Ton
(74) *Attorney, Agent, or Firm* — Linda B. Huber; Nixon Peabody LLP (57) ABSTRACT

A plasmonic structure (10) comprising a layer of metal (14) in which the metal is selected from: a Group 8 to Group 11 transition metal, aluminum, germanium, antimony or bismuth, and a barrier layer (16) formed from a 2-D material disposed on a surface of the layer of metal (14). The metal layer has a roughness that permits the propagation of running plasmons along the interface of the metal layer and the barrier layer.

15 Claims, 6 Drawing Sheets

(51) Int. Cl.
*G02B 6/122* (2006.01)
*G02B 6/132* (2006.01)
*G02B 6/12* (2006.01)

(58) Field of Classification Search
USPC .................................................. 356/432–448
See application file for complete search history.

(56) References Cited

OTHER PUBLICATIONS

Choi et al., Graphene-on-Silver Substrates for Sensitive Surface Plasmon Resonance Imaging Biosensors, Opt. Express, 2011, vol. 19(2), pp. 458-466.
Salihoglu et al., Plasmon-Polaritons on Graphene-Metal Surface and their Use in Biosensors, Applied Physics Letters, 2012, vol. 100(21), pp. 213110-1-213110-6.
Liedberg et al., Surface Plasmon Resonance for Gas Detection and Biosensing, Sensors and Actuators, 1983, vol. 4, pp. 299-304.
Nagpal et al., Ultrasmooth Patterned Metals for Plasmonica and Metamaterials, Science, 2009, vol. 325(5940), pp. 594-597.
Homola J., Surface Plasmon Resonance Sensors for Detection of Chemical and Biological Species, Chemical Reviews, 2008, vol. 108(2), pp. 462-493.
GB Application No. 1408727.4 Search Report Under Section 17(5) dated Nov. 18, 2014, 5 pages.
Zuccon et al., Functional Palladium Metal Films for Plasmonic Devices: An Experimental Proof, Journal of Optics, 2014, vol. 16(5), pp. 1-7.
Cittadini et al., Graphene Oxide Coupled with Gold Nanoparticles for Localized Surface Plasmon Resonance Based Gas Sensor, Carbon, 2014, vol. 69, pp. 452-459.
Maharana et al., Sensetivity Enhancement by Air Mediated Graphene Multilayer Based Surface Plasmon Resonance Biosensor for Near Infrared, Sensors and Actuators B (Chemical), 2014, vol. 190, pp. 494-501.
GB Application No. 1408727.4 Search Report Under Section 17(6) dated Sep. 24, 2015; 2 pages.
GB Application No. 1408727.4 Search Report Under Section 17(6) dated Sep. 30, 2015; 2 pages.
Park et al., Simple, Green and Clean Removal of a Poly(Methyl Methacrylate) Film on Chemical Vapor Deposited Graphene, Applied Physics Letters, 2013, vol. 103(17), pp. 171609-1-17609-4.

\* cited by examiner

PLASMONIC STRUCTURES AND DEVICES

CROSS-REFERENCE TO RELATED APPLICATIONS

This application is a National Phase of International Application No. PCT/GB2015/051432 filed May 14, 2015, which designated the U.S. and that International Application was published under PCT Article 21(2) in English. Both applications also include a claim of priority under 35 U.S.C. § 119(a) and § 365(b) to British patent application No. GB 1408727.4 filed May 16, 2014, the entirety of which is hereby incorporated by reference.

The present invention relates to improved plasmonic structures, devices and methods associated therewith.

BACKGROUND

Plasmonics has established itself as a branch of physics which, among other applications, has the potential to revolutionize data processing, improve photovoltaics, and increase sensitivity of bio-detection. Plasmonics generally relates to the interaction between light and electron plasma oscillations in metals. Surface plasmons are coherent oscillations of free electrons that exist at an interface between two materials where the real part of the dielectric function changes sign across the interface (e.g. a metal-dielectric interface).

Gold is the current metal of choice for plasmonic applications due to its strong plasmonic response. However, gold is not compatible with standard silicon manufacturing processes (e.g. complementary metal oxide semiconductor (CMOS) technology) due to an efficient diffusion of gold into silicon. This incompatibility, together with the relatively high cost of gold, has hindered the widespread use and adoption of plasmonic devices.

There is an on-going search for inexpensive alternative materials that may replace gold for plasmonic applications and make plasmonic devices more economically attractive.

In one numerical (i.e. theoretical) study (Choi et al; Graphene-on-silver substrates for sensitive surface plasmon resonance imaging biosensors. Optics Express, 17 Jan. 2011, Vol. 19, No. 2, 458) it is hypothesized that a silver film coated in graphene may improve the sensing performance of a silver-based surface plasmon resonance (SPR) imaging biosensor beyond that of an equivalent gold-based SPR imaging biosensor. However, experimental attempts to date have not resulted in a device that possesses the desired plasmonic response required to make a functional plasmonic device. As an example, Salihoglu et al. (Plasmon-polaritons on graphene-metal surface and their use in biosensors. Applied Physics Letters, 23 May 2012, vol. 100, 213110) reports an experimental attempt to use graphene coated silver for use in a plasmonic device. However, it was found that the addition of the graphene to the silver significantly degraded the plasmonic response of the material.

There still exists a need, therefore, for alternative plasmonic structures that will enable commercially viable plasmonic devices.

It is an aim of certain embodiments of the present invention to provide a plasmonic structure that is resistant to oxidation.

Another aim of certain embodiments of the present invention is to provide a plasmonic structure that may function in a wet environment.

A further aim of certain embodiments of the present invention is to provide a plasmonic structure that is compatible with complementary metal oxide semiconductors (CMOS) and CMOS fabrication methods.

It is also an aim of certain embodiments of the present invention to provide a plasmonic structure that is functionalized for biological applications.

Another aim of certain embodiments of the present invention is to provide a plasmonic structure that is convenient and/or inexpensive to manufacture.

The present invention satisfies some or all of the above aims.

BRIEF SUMMARY OF THE DISCLOSURE

In accordance with one aspect of the present invention there is provided a plasmonic structure comprising:
  a layer of metal in which the metal is selected from: a Group 8 to Group 11 transition metal, aluminium, germanium, antimony or bismuth; and
  a barrier layer formed from a 2-D material disposed on a surface of the layer of metal;
  wherein the metal layer has a roughness that permits the propagation of running plasmons along the interface of the metal layer and the barrier layer.

In accordance with the invention, the layer of metal can therefore be selected from: iron, cobalt, nickel, ruthenium, rhodium, palladium, silver, osmium, iridium, platinum, copper, silver, gold, aluminium, germanium, antimony, or bismuth.

In certain embodiments of the plasmonic structure, the layer of metal is selected from: copper, silver, or aluminium. In some cases, the layer of metal is copper since this can be advantageous when producing plasmonic devices. Using aluminium as the layer of metal can also be advantageous when producing plasmonic devices. Similarly, the use of silver can also be technically beneficial when producing plasmonic devices. The layer of metal may be selected from a Group 8 to Group 11 transition metal, and the metal is frequently chosen from Group 11.

In alternative embodiments of the plasmonic structure, the layer of metal is a metal other than copper which is selected from: a Group 8 to Group 11 transition metal, aluminium, germanium, antimony or bismuth. Similarly, in these alternative embodiments, the layer of metal is aluminium since this can be advantageous when producing plasmonic devices. Using silver as the layer of metal can also be advantageous when producing plasmonic devices.

In alternative embodiments of the plasmonic structure, the layer of metal is a metal other than gold and/or palladium and/or platinum which is selected from: a Group 8 to Group 11 transition metal, aluminium, germanium, antimony or bismuth. In these embodiments, the effects of any instability in the layer of metal on the plasmonic properties of the plasmonic structure may be significantly reduced by the inclusion of the barrier layer.

The function of the barrier layer is to prevent or substantially hinder access of water, oxygen/air, or other chemical contaminants such as hydrocarbons, oxides of nitrogen, oxides of sulphur and oxides of carbon etc. to the surface of the metal layer. Reaction with one or more of these aforementioned contaminants may in some cases have a detrimental effect on the properties of the metal surface and in particular on the roughness of the metal surface. This is due to a chemical reaction between water, oxygen/air, and/or any other chemical contaminants which might be present in the vicinity of the structure. In the present invention, the barrier layer eliminates or substantially reduces any degradation of the metal surface due to the presence of such contaminants.

Accordingly, any 2-D barrier material which is able to protect and maintain the surface qualities of the metal layer from external contamination is suitable in the present invention. Graphene is particularly advantageous since it provides an effective barrier. Similarly, hexagonal boron nitride (hBN) provides an effective barrier layer. Other 2-D materials are suitable to the extent that they perform the same function of excluding chemical contaminants and maintaining the integrity of the metal layer. The barrier layer itself may be a single layer 2-D material (which itself is present as a single layer or a few atomic layers of material which typically will be less than 20 or 10 or 5 atomic layers of the 2-D material). In this context, the reference to a single "layer" of 2-D material refers to a single piece of the 2-D material which may or may not comprise only a single i.e. monolayer of atoms or maybe a few atomic layers thick. Alternatively, the barrier layer may be made up of more than one layer of 2-D material (each "layer" of the 2-D material itself comprising a single layer or a few atomic layers of the particular 2-D material). When the barrier layer is formed from more than one layer of 2-D material, such that the barrier layer is effectively a laminate of 2-D materials, the various component layers of the barrier layer may be formed from the same 2-D material or from different 2-D materials.

Thus, the plasmonic structure may have as its barrier layer a material selected from one or more of: graphene, reduced graphene oxide, BN, $MoS_2$, $MoSe_2$, $MoTe_2$, $W5_2$, $WSe_2$, $WTe_2$, $TaS_2$, $NbSe_2$, $NbS_2$, $ReS_2$, $ReSe_2$, $TiS_2$, $TiSe_2$, black phosphorous, graphene, or fluorinated graphene.

The layer of metal can be deposited by conventional techniques and may be presented in the form of a film or a coating. In certain embodiments, the layer of metal is a film. In some embodiments, the layer of metal is an electron-beam evaporation grown layer or a sputtered layer. Alternatively, the barrier layer may be a chemical vapour deposition (CVD) grown layer.

In certain embodiments of the plasmonic structure, the barrier layer includes graphene that is mechanically exfoliated prior to transfer onto the surface of the layer of metal. Mechanical exfoliation can be conducted in a variety of different ways and graphene produced by any of the currently available or other suitable mechanical techniques are suitable for the present invention. One recently described process that can be used in accordance with the present invention involves exfoliation using a shearing force generated by a rapidly rotating tool in solution to separate the layers of graphene from graphite flakes. Similarly, layers of other 2-D materials that are to be used as the barrier layer in the present invention can also be produced by equivalent mechanical means to those used for graphene. These methods have the benefit of preserving the two-dimensional structure of the material.

The present invention also relates to a plasmonic device including the plasmonic structure described in any of the above embodiments. Particular features i.e. embodiments described above in relation to the plasmonic structure also apply in relation to the plasmonic device.

Such a plasmonic device may in certain embodiments comprise a light source arranged relative to the plasmonic structure to excite surface plasmons in the plasmonic structure. The plasmonic device may also further comprise a detector.

In embodiments in which detector is provided, the detector is configured to detect a property of light following an interaction of the light with the plasmonic structure. One application of a plasmonic device in accordance with the invention is as a surface plasmon resonance (SPR) device configured to measure the SPR response of the plasmonic structure.

In embodiments where the plasmonic device is an SPR device, the plasmonic structure may be mounted on a prism in a Turbadar-Kretschmann-Raether configuration. In such embodiments the plasmonic structure may exhibit a reflectance of incident light at a wavelength between 100 nm and 1000 nm of 20% or less, or 10% or less. In embodiments where the plasmonic device is an SPR device, the plasmonic structure may have a quality factor Q of at least 19, or at least 20, for a SPR ellipsometric curve of the plasmonic structure, where $Q=\lambda_R/(\Delta\lambda_{FWHM})$ and $\lambda_R$ is the resonance wavelength corresponding to the SPR minimum and $\Delta\lambda_{FWHM}$ is the full-width of the resonance at half-minimum of the SPR ellipsometric curve.

In some embodiments, the plasmonic device may further comprise a dielectric-loaded surface plasmon-polariton waveguide (DLSPPW), wherein the plasmonic structure forms part of the DLSPPW.

In certain embodiments, the plasmonic device may further include a complementary metal-oxide semiconductor (CMOS).

In some embodiments, the plasmonic device may be a biosensor for measuring one or more properties of an analyte, wherein, optionally, the analyte is receivable on the barrier layer, and is preferably bindable to the barrier layer.

The invention also concerns a method of making a plasmonic structure. In general terms, the method of making the plasmonic structure comprises the steps of:
 providing a layer of metal;
 providing a layer of graphene;
 coating the layer of graphene in a carrier layer;
 transferring the coated layer of graphene onto the layer of metal; and
 removing the carrier layer to leave a layer of graphene disposed on the layer of metal.

Particular features i.e. embodiments described above in relation to the plasmonic structure also apply in relation to the method.

In accordance with the invention, the layer of metal can therefore be selected from: iron, cobalt, nickel, ruthenium, rhodium, palladium, silver, osmium, iridium, platinum, copper, silver, gold, aluminium, germanium, antimony, or bismuth.

In certain embodiments, the metal is selected from: copper, silver, or aluminium. In some cases, the layer of metal is copper since this can be advantageous when producing plasmonic devices. Using aluminium as the layer of metal can also be advantageous when producing plasmonic devices. Similarly, the use of silver can also be technically beneficial when producing plasmonic devices.

Further features and embodiments of the plasmonic structure, plasmonic device, and method of the invention are described in the claims.

In accordance with an aspect of the present invention, there is provided a method of making a plasmonic structure comprising the steps of:
 providing a layer of copper;
 providing a layer of graphene;
 coating the layer of graphene in a carrier layer;
 transferring the coated layer of graphene onto the layer of copper; and
 removing the carrier layer to leave a layer of graphene disposed on the layer of copper.

The layer of graphene may be provided by mechanically exfoliating graphite.

Alternatively, the layer of graphene may be provided by chemical vapour deposition (CVD) growth.

The graphene may be grown on an auxiliary layer of copper prior to the steps of coating the layer of graphene with the carrier layer and transferring the coated layer of graphene onto the layer of copper. The auxiliary layer of copper may be annealed to remove or substantially reduce a native oxide layer therefrom prior to growth of graphene on the auxiliary layer of copper. The step of annealing may include heating the auxiliary layer of copper to a temperature between 900° C. and 1100° C. for between 25 and 35 minutes, and preferably at about 1000° C. and/or preferably for about 30 minutes. The auxiliary layer of copper may be removed from the coated layer of graphene prior to the step of transferring the coated layer of graphene onto the layer of copper. In particular, the auxiliary layer of copper may be removed from the coated layer of graphene by chemical etching.

The layer of copper may be provided by electron beam evaporation growth. 99.99% Cu may form an electron-beam target material for the growth of the layer of copper. The layer of copper may be grown on an adhesion layer of chromium. Electron-beam evaporation may be performed at a base pressure of between $0.8 \times 10^{-7}$ mbar and $1.2 \times 10^{-7}$ mbar, and preferably about $1 \times 10^{-7}$ mbar. The layer of copper may be grown at a thickness rate between 0.2 nm/s and 0.4 nm/s, and preferably about 0.3 nm/s.

In alternative embodiments, the layer of copper is provided by sputtering.

The method may further comprise fabricating a dielectric waveguide structure on the layer of graphene disposed on the film of copper. The dielectric waveguide structure may be fabricated by photolithography.

The carrier layer may comprise poly(methyl methacrylate) (PMMA), wherein the layer of graphene may be coated in PMMA by spin coating. The step of removing the PMMA may be performed using acetone.

The method may further comprise the steps of:
providing a further layer of graphene;
coating the further layer of graphene in a carrier layer;
transferring the coated further layer of graphene onto the layer of graphene disposed on the layer of copper; and
removing the carrier layer to leave the further layer of graphene on the layer of graphene disposed on the layer of copper.

In accordance with another aspect of the present invention, there is provided a method of making a plasmonic device, including the steps of providing a plasmonic structure made according to any of the above-described methods of making a plasmonic structure using a layer of copper, and providing a light source and arranging the light source relative to the plasmonic structure to excite surface plasmons in the plasmonic structure.

In accordance with another aspect of the present invention, there is provided a method of making a plasmonic device, including the steps of making a plasmonic structure according to any of the above-described methods of making a plasmonic structure using a layer of copper, and providing a light source and arranging the light source relative to the plasmonic structure to excite surface plasmons in the plasmonic structure.

In accordance with another aspect of the present invention, there is provided a method of making a plasmonic structure comprising the steps of:
providing a layer of silver;
providing a layer of graphene;
coating the layer of graphene in a carrier layer;
depositing a solvent onto the layer of silver, where the solvent does not cause oxidation of the silver;
transferring the coated layer of graphene onto the layer of silver by placing the coated layer of graphene on the deposited solvent and allowing the solvent to evaporate; and
removing the carrier layer to leave a layer of graphene disposed on the layer of silver.

The carrier layer may be heated after the layer of graphene is placed on the deposited solvent and prior to the step of removing the carrier layer.

In certain embodiments, the temperature does not exceed 70° C. throughout the method, and preferably the temperature does not exceed 50° C. throughout the method.

Remaining solvent may be pumped away prior to removing the carrier layer.

The layer of graphene may be provided by mechanically exfoliating graphite. In such embodiments, any silicon remaining from the mechanical exfoliation of graphite may be removed from the coated layer of graphene prior to the step of transferring the coated layer of graphene onto the layer of silver. The silicon may be removed from the coated layer of graphene by chemical etching.

In other embodiments, the layer of graphene may be provided by chemical vapour deposition (CVD) growth. The graphene may be grown on an auxiliary layer of copper prior to the steps of coating the layer of graphene with the carrier layer and transferring the coated layer of graphene onto the layer of silver. The auxiliary layer of copper may be annealed to remove or substantially reduce a native oxide layer therefrom prior to growth of graphene on the auxiliary layer of copper. The step of annealing may include heating the auxiliary layer of copper to a temperature between 900° C. and 1100° C. for between 25 and 35 minutes, and preferably at about 1000° C. and/or preferably for about 30 minutes. The auxiliary layer of copper may be removed from the coated layer of graphene prior to the step of transferring the coated layer of graphene onto the layer of silver. The auxiliary layer of copper may be removed from the coated layer of graphene by chemical etching.

In certain embodiments, the layer of silver may be provided by electron beam evaporation growth.

In other embodiments, the layer of silver may be provided by sputtering.

The method may further comprise fabricating a dielectric waveguide structure on the layer of graphene disposed on the layer of silver. The dielectric waveguide structure may be fabricated by photolithography.

The carrier layer may comprise poly(methyl methacrylate) (PMMA). The step of removing the PMMA may be performed using acetone.

The method may further comprise the steps of:
providing a further layer of graphene;
coating the further layer of graphene in a carrier layer;
transferring the coated further layer of graphene onto the layer of graphene disposed on the layer of silver; and
removing the carrier layer to leave the further layer of graphene on the layer of graphene disposed on the layer of silver.

It is important to appreciate that features of the various embodiments described above in relation to the plasmonic structure, plasmonic device and method of making these may be used in combination with one another such that one, two, or several of the above embodiments may be used in any combination with one another.

BRIEF DESCRIPTION OF THE DRAWINGS

Embodiments of the invention are further described hereinafter with reference to the accompanying drawings, in which.

DETAILED DESCRIPTION

Aspects of the present invention relate to functional plasmonic structures and devices that may be produced with metals selected from a Group 8 to Group 11 transition metal, aluminium, germanium, antimony or bismuth. Other aspects of the present invention relate to associated methods for manufacturing such structures and devices. Plasmonic devices made in accordance with the present invention are found to show excellent plasmonics characteristics, which, in certain embodiments, surpass those of the gold-based devices of the prior art. Moreover, plasmonic devices in accordance with certain aspects of the present invention are stable over long periods of time, even in wet and/or corroding conditions, making them particularly suitable for biosensor applications.

In one aspect of the present invention, there is provided a plasmonic structure that is formed of a layer (which may be a film) of metal, where the metal is selected from a Group 8 to Group 11 transition metal, aluminium, germanium, antimony or bismuth, and a barrier layer disposed on the surface of the layer of metal. The barrier layer is formed from a 2-D material that may be include one or more of: graphene, reduced graphene oxide, BN, $MoS_2$, $MoSe_2$, $MoTe_2$, $WS_2$, $WSe_2$, $WTe_2$, $TaS_2$, $NbSe_2$, $NbS_2$, $ReS_2$, $ReSe_2$, $TiS_2$, $TiSe_2$, black phosphorous, graphane, or fluorinated graphene. The barrier layer may be a single layer of the 2-D material or a laminate comprising a plurality of the 2-D materials where the plurality of 2-D materials may be the same or different to one another.

The chosen barrier layer preferably has one or more of the following preferable characteristics: impermeability to oxygen, impermeability to water, chemical inertness, low optical absorbance so as to be useful optically, extremely low thickness, and strong affinity to metals. In certain embodiments, the barrier layer has a thickness that is smaller than the exponential decay length of the electromagnetic fields near the interface between the layer of metal and the barrier layer. For example, in certain embodiments, the thickness of the barrier layer should be less than $\lambda_0/10$, where $\lambda_0$ is the wavelength of the incident light in free space or studied environment (e.g., water).

The metal is preferably substantially free of oxides and/or other contaminants both before and after transfer of the barrier layer (if the barrier layer is being transferred). Therefore, the transfer procedure itself should not cause oxidation and/or other contamination of the metal. Once transferred (or otherwise disposed on the metal), the barrier layer is arranged on the layer of metal so as to protect the layer of metal from oxidation and/or other contamination. It is found that oxidation of the layer of metal introduces inhomogeneity on the surface of the metal (e.g. by the formation of large grains). Such inhomogeneity may increase surface roughness (amongst other effects) and degrade the plasmonic response of the metal by increasing scattering and absorption of running plasmons. Thus, maintenance of the structural integrity of the metal layer in terms of its surface roughness and/or relative lack of chemical impurities is an important feature of the present invention.

The relative importance of the surface roughness effect and the avoidance of chemical impurities in securing effective running plasmons varies from metal to metal. In other words, both factors are important but their importance differs according to the metal that is being used as the plasmonic material.

Importantly, the surface of the layer of metal has a roughness that permits the propagation of running surface plasmons along the interface of the layer of metal and the barrier layer. As is discussed further below with reference to experimental evidence, heating may cause an increase in surface roughness, and surface roughness is found to be a relevant factor in the plasmonic response of a material. Therefore, by producing a layer of metal (e.g. copper) that remains substantially free of oxides (e.g. copper oxide) and that possesses a roughness (following fabrication of the plasmonic structure) that permits the propagation of running surface plasmons along the interface of the layer of the metal and the barrier layer, a plasmonic structure may be provided such that a light source may be used to excite surface plasmons therein to provide a functional plasmonic device. Running surface plasmons are distinct from localized surface plasmons in that running surface plasmons are able to propagate and therefore be useful in information processing, optical communications, optoelectronics and sensing.

Running surface plasmons are electromagnetic surface waves propagating along the metal surface with a broad spectrum of eigen-frequencies depending on the propagating wave number/vector. They represent solutions of Maxwell equations, i.e. a combined propagating mode of vibrations of electron plasma of metals with electromagnetic field near the metal surface.

In contrast, a localized surface plasmon is produced by the confinement of electron plasma vibrations in a nanostructure (e.g. a nanoparticle) having a size comparable to or smaller than the wavelength of light used to excite the plasmon. The localized surface plasmons do not propagate and are described by virtual photons and near-fields. As such, localized surface plasmons do not have an associated wave number/vector.

The propagation wavenumber of running surface plasmons (or "surface plasmon polaritons" in the case of a metal-dielectric interface) can be evaluated as $$k = k_0 \sqrt{\frac{\varepsilon_m \varepsilon_d}{\varepsilon_m + \varepsilon_d}} \approx k_0 \sqrt{\varepsilon_d},$$

where $k_0$ is the wavenumber of the light, $\varepsilon_m$ is the permittivity of metal and $\varepsilon_d$ is the permittivity of dielectric. In typical cases $$k \sim \frac{2\pi}{\lambda_0}$$

and hence the wavelength of running surface plasmons is around the wavelength of exciting light.

In the presence of roughness, there are two additional processes of plasmon decay, namely: (i) radiation losses connected with transition of running surface plasmon waves into photons emitted into the dielectric; and (ii) scattering of running surface plasmons into running surface plasmon waves of different directions. The Gaussian roughness of a metal-dielectric interface with a correlation function may be expressed as:

$$G(x, y) = \delta^2 \exp\left(-\frac{x^2 + y^2}{\sigma^2}\right),$$

for orthogonal x and y directions where $\sigma$ is the corrugation length and $\delta$ is the corrugation strength (the Gaussian nature of the corrugations is often observed experimentally). For a fabricated layer of metal, the corrugation length relates to the size of grains of the metal layer, while the corrugation strength is connected to the root mean square of the surface roughness.

Process (i) has an associated mean free path for radiation losses, $L_{rad}$, that can be expressed as:

$$L_{rad} = \frac{3}{4} \frac{|\varepsilon'_m|^{1/2}}{k_0^5} \frac{1}{\sigma^2 \delta^2}.$$

Process (ii) has an associated mean free path for running surface plasmon scattering, $L_{sc}$, that can be expressed as:

$$L_{sc} = \frac{2}{3} \frac{|\varepsilon'_m|}{k_0^5} \frac{1}{\sigma^2 \delta^2},$$

(assuming that $|\varepsilon'_m| \gg 1$). Hence radiation losses dominate and the mean free path due to roughness, L, is around:

$$\frac{L}{\lambda_0} \approx \frac{|\varepsilon'_m|^{1/2}}{(2\pi)^5} \frac{\lambda_0^4}{\sigma^2 \delta^2}.$$

In certain embodiments, roughness may be considered low enough to permit the propagation of running surface plasmons along the interface of the metal layer and the barrier layer when $$\frac{L}{\lambda_0} \gg 1$$

(in which propagation of running surface plasmons is limited by the internal decay length defined by the imaginary part of metal permittivity). In certain embodiments, $L/\lambda_0$ may be greater than 1, 2, 5, or 10. In certain embodiments, roughness may be considered too great to permit the propagation of running surface plasmons along the interface of the metal layer and the barrier layer when $$\frac{L_{sc}}{\lambda_0} \leq 1$$

(at which point the propagation of running surface plasmons may be strongly inhibited). High roughness is realised when both the corrugation strength and the corrugation length are of the order of the wavelength of exciting light. If, for example, the corrugation length of a sample is increased to 10 times larger than the wavelength of exciting light then the corrugation strength should be 10 times smaller if propagation of running surface plasmons is to be maintained with the same degree of losses.

In accordance with the present invention, functional plasmonic devices have been produced using copper coated with graphene and silver coated with graphene. In contrast with the unsuccessful attempts of the prior art, a functional silver-graphene-based plasmonic device may be provided by ensuring that the silver is substantially free of silver oxide and has a roughness that permits the propagation of running surface plasmons along the interface of the film of silver and the graphene. As is described in further detail below, these principles may be applied to certain plasmonic structures incorporating a layer of metal, where the metal is any metal selected from: a Group 8 to Group 11 transition metal, aluminium, germanium, antimony or bismuth.

Throughout the present specification, the term "substantially free of oxides" (and equivalent terms) means a surface which is oxidised, i.e. is coated with or composed of an oxide, over a sufficiently small area so that the material surface still allows successful propagation of running plasmons (i.e. the decay and scattering lengths of plasmons are larger than the plasmon wavelength).

The preferable roughness may be characterized with reference to the root mean square of the roughness of the surface of the layer of metal. Here, root mean square of the roughness ($R_q$) is defined as $$R_q = \sqrt{1/L \int_0^L z^2(x)dx},$$

where L is the evaluation length, and z(x) is the height at position x. The root mean square of the roughness of a surface may be readily measured and determined by any suitable method in the art. For example, optical methods (such as interferometry) or atomic force microscopy (AFM) may be used to measure the root mean square of the roughness of a surface.

It is found that, in plasmonic structures in accordance with the present invention, the maximum root mean square of the roughness of the metal layer that permits the propagation of running plasmons at the interface of the metal layer and the barrier layer (e.g. graphene) is dependent on the wavelength of incident light. In one example, where the incident light is in the visible part of the spectrum (i.e. having a wavelength between 390 nm and 700 nm), the root mean square of the roughness of the surface of the film of metal is less than 50 nm or, further preferably, less than 20 nm. It is found that the lower the value of the root mean square of the roughness of the surface of the layer of metal, the stronger the plasmonic characteristics.

Importantly, whilst a layer of metal that possesses these features may be provided prior to the transfer of the barrier layer, the fabrication process must be such that the metal of the resulting metal-barrier layer structure also possesses these features (i.e. the fabrication process itself must not cause an increase in roughness such that the propagation of running surface plasmons is no longer permitted).

Considering embodiments of the invention where the barrier layer is graphene, whilst the invention is not necessarily limited to such, preferable results are obtained when the graphene is not grown directly on the layer of metal that forms part of the plasmonic structure. Instead, graphene may be provided separately and then transferred onto a layer of metal. The graphene may be produced by mechanical exfoliation of graphite, by chemical vapour deposition (CVD) (e.g. on an auxiliary layer of copper) or by any other suitable production method before being transferred onto the layer of metal of the plasmonic structure.

Considering copper, a layer (e.g. a film) of copper may be produced by electron-beam evaporation of copper onto a substrate. In alternative embodiments, the layer of copper (or, indeed, other metal in accordance with the present invention) may be produced by any other suitable method, including, but not limited to, sputtering. In certain embodiments, the electron-beam evaporation of copper may be performed at a base pressure between $0.8 \times 10^{-7}$ mbar and $1.2 \times 10^{-7}$ mbar, and preferably about $1 \times 10^{-7}$ mbar. The growth rate of copper (i.e. with respect to its thickness) may be between 0.2 nm/s and 0.4 nm/s in certain embodiments, and may preferably be about 0.3 nm/s. In one specific example, the electron-beam target is 99.99% copper. In certain embodiments, a thin layer of chromium may be evaporated onto the substrate (e.g. around 1.5 nm thick) prior to growth of the copper film, where the chromium layer may assist adhesion of the copper. Any suitable substrate may be used, although glass substrates are particularly suitable. The substrates may be cleaned (in heated acetone and isopropanol, for example) prior to deposition.

Separately, graphene is provided for transfer onto the film of copper. As noted above, graphene may be produced by mechanical exfoliation of graphite, or it may be grown by CVD or any other suitable process. For the CVD method, the graphene may be grown on an auxiliary layer of copper. The CVD method of producing the graphene may include the step of heating an auxiliary layer of copper in a quartz tube with flowing hydrogen gas. In a specific non-limiting example, the auxiliary layer of copper is placed in the quartz tube and heated to 1000° C. with $H_2$ gas flowing at a rate of 20 cm$^3$/min and a pressure of 200 mTorr. To remove the native oxide layer from the auxiliary layer of copper, the auxiliary layer of copper may first be annealed (e.g. at around 1000° C. for about 30 minutes). A gas mixture of $H_2$ and $CH_4$ may then be introduced into the quartz chamber. In a specific example, $H_2$ and $CH_4$ are introduced at flow rates of 20 and 40 cm$^3$/min, respectively, and CVD growth is performed at a pressure of 600 mTorr for 30 minutes. Finally, the CVD chamber may be rapidly cooled to room temperature in a hydrogen atmosphere. Graphene grown in accordance with these methods may be predominantly single-layer graphene and may preferably be predominantly single-layer graphene with a low occurrence of defects.

In order to transfer the graphene onto the film of copper, a layer of poly(methyl methacrylate) (PMMA) (or other suitable carrier layer) is first applied to the graphene (e.g. by spin coating). If CVD graphene is used, the auxiliary layer of copper may then be removed by chemical etching to leave the PMMA coated graphene. In the case where mechanically exfoliated graphene is used, a layer of silicon (which is used in the mechanical exfoliation process) may be etched away from the graphene to leave just the graphene with the PMMA coating. In either case, the PMMA coated graphene is transferred onto the film of copper that is to form part of the plasmonic structure. The positioning of the PMMA coated graphene onto the film of copper may be aided by visual inspection (e.g. using an optical microscope). Finally, the PMMA layer may be removed (e.g. using acetone) and the graphene surface may be cleaned further (e.g. by annealing in hydrogen at 200° C. for 60 minutes, for example). The result of the process is a plasmonic structure that includes a film of copper with a layer of graphene disposed thereon, where the copper remains substantially oxide free and has a roughness that permits the propagation of running surface plasmons along the interface of the film of copper and the graphene. As such, the plasmonic structure may be used in a plasmonic device that represents a viable alternative to conventional gold-based devices.

With regards to the silver-based plasmonic structure in accordance with aspects of the present invention, where the barrier layer is graphene, the graphene may be produced by mechanical exfoliation of graphite or CVD growth. In particular, the graphene for the silver-based plasmonic structure may be produced according to the methods described above in relation to the copper-based plasmonic structure. However, the transfer procedure for silver differs from that of copper, at least partly due to the greater propensity of silver to oxidise. The graphene is first covered with PMMA (e.g. a layer of PMMA around 400 nm thick) or another suitable carrier layer. A tape window may be cut out and placed on the PMMA to provide a visual marker (e.g. following a subsequent etching step). For CVD derived graphene, the auxiliary layer of copper is etched away. This may be achieved using 0.1 Mol ammonium persulfate for around 6 hours, for example. In the case of mechanically exfoliated graphene, the silicon layer may be etched away at this stage.

Etching of the auxiliary layer of copper or silicon leaves a layer of PMMA coated graphene. The PMMA coated graphene may be cleaned (e.g. in deionized water) to remove contamination from etchant solution and then dried. Drying may be achieved by leaving the PMMA coated graphene in ambient conditions (e.g. for around 10 minutes). The graphene must then be transferred and adhered to a layer (which may be a film) of silver without causing or allowing the film of silver to oxidise. In accordance with an aspect of the present invention, a solvent that is capable of evaporating but not oxidizing the layer of silver is then added to the surface of the film of silver, and the PMMA coated graphene is placed on the solvent. Suitable solvents include isopropyl alcohol (IPA). As the solvent evaporates, the resulting capillary action assists the adhesion of the PMMA coated graphene to the layer of silver thereby obviating the need for heating which would lead to oxidation and degradation of plasmonic properties. Once the PMMA covered graphene is suitably adhered to the layer of silver, the PMMA may be removed (e.g. in acetone). Optionally, any remaining solvent may be pumped away using a vacuum. Additionally or alternatively, the PMMA may be gently heated to soften the PMMA and assist subsequent removal. However, any heating must not cause oxidation of the layer of silver which would lead to degradation of the plasmonic properties. In one example, the PMMA coated graphene (on the film of silver) is heated to around 50° C. for about 30 minutes to soften the PMMA. Following removal of the PMMA, the graphene coated layer of silver may be rinsed in IPA and subsequently dried (e.g. in nitrogen).

The resulting plasmonic structure includes a layer of silver with a layer of graphene disposed thereon, where the silver remains substantially oxide free and has a roughness that permits the propagation of running surface plasmons along the interface of the film of silver and the graphene. As such, the plasmonic structure may be used in a plasmonic device that represents a further viable alternative to conventional gold-based devices.

Figure 8:
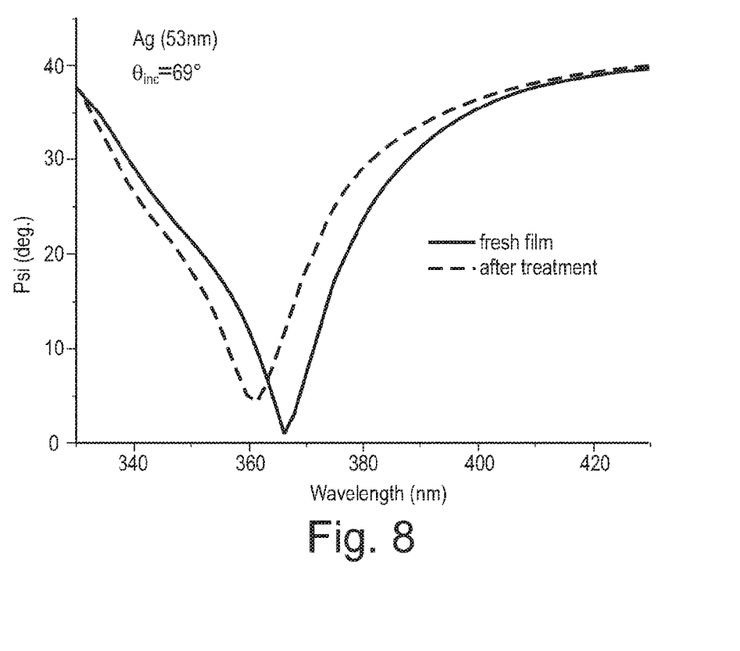
FIG. 8 shows the SPR ellipsometric reflection for a film of silver (53 nm thick) both before and after mild heat treatment.
Figure 9A:
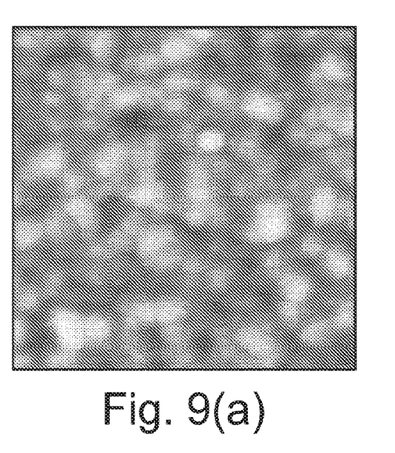
FIG. 9(a) shows a 2×2 µm micrograph of the surface of a film of silver prior to heat treatment.
Figure 9B:
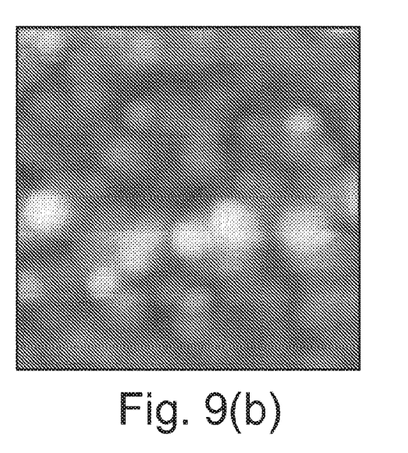
FIG. 9(b) shows a 2×2 µm micrograph of the surface of a film of silver after heat treatment.

FIG. 8 demonstrates the detrimental effect of heating on the plasmonic properties of a film of (unprotected) silver. In particular, FIG. 8 shows the SPR ellipsometric reflection for a film of silver (53 nm thick) both before and after mild heat treatment (to around 100° C.) from which it can be seen that the plasmonic response has declined following heat treatment. FIG. 9(a) shows a 2×2 µm micrograph of the surface of the film of silver prior to heat treatment and FIG. 9(b) shows a 2×2 µm micrograph of the surface of the film of silver after heat treatment. By comparing FIG. 9(b) to FIG. 9(a), it can be seen that the surface roughness has increased following heat treatment. Analysis of the samples shows that the root mean square (rms) value of the surface roughness of the silver prior to heat treatment is 3.4 nm and 5.2 nm following the mild heat treatment. FIGS. 8, 9(a) and 9(b) demonstrate the effects of oxidation and roughness on the plasmonic properties of materials. In particular, plasmonic properties are inhibited as the roughness of the metal increases.

Figure 1:
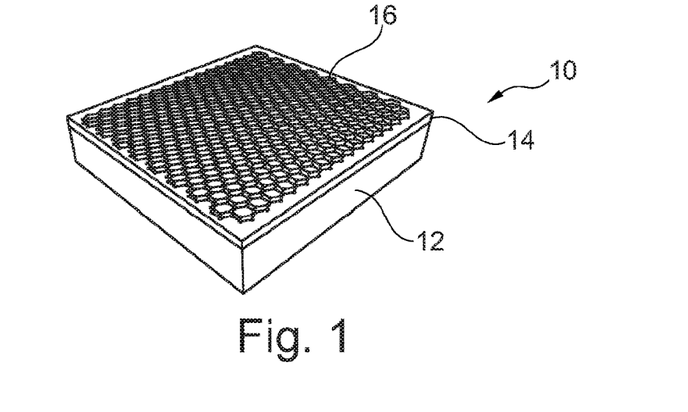
FIG. 1 shows a plasmonic structure in accordance with an embodiment of the present invention.

An example of a plasmonic structure 10 in accordance with an embodiment of the present invention is shown in FIG. 1. The plasmonic structure 10 includes a film of copper 14 on a substrate 12 with a layer of graphene 16 disposed on the layer of copper 14.

Figure 2:
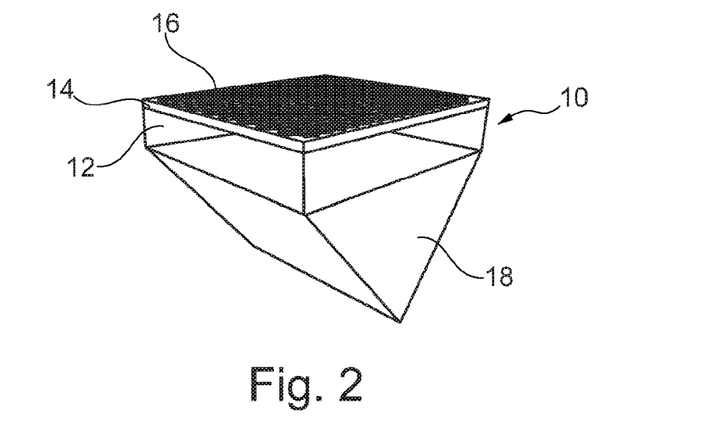
FIG. 2 shows the plasmonic structure of FIG. 1 mounted on a prism in the Turbadar-Kretschmann-Raether configuration.

FIG. 2 shows an example where the plasmonic structure 10 of FIG. 1 is mounted on a prism 18 in the Turbadar-Kretschmann-Raether configuration. This configuration is particularly suitable for measuring the surface plasmon resonance (SPR) of the plasmonic structure 10.

Figure 3:
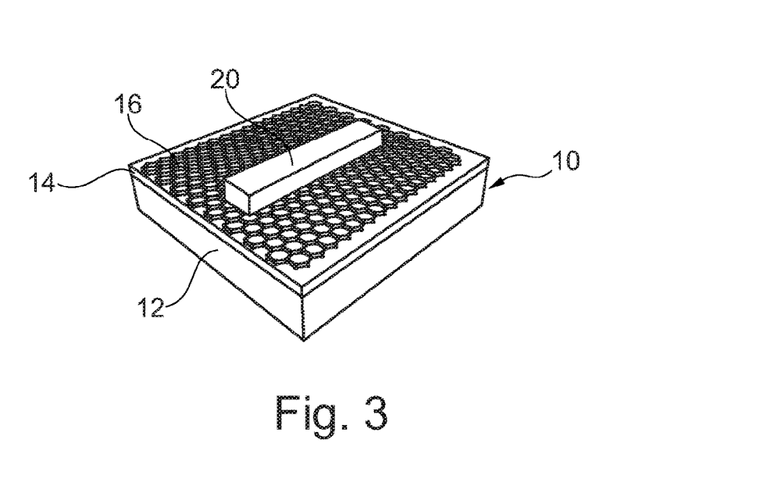
FIG. 3 shows the plasmonic structure of FIG. 1 with a dielectric waveguide disposed on the surface of the graphene.

FIG. 3 shows the plasmonic structure 10 of FIG. 1 with a dielectric waveguide 20 disposed on the surface of the graphene 16 where the dielectric waveguide 20 forms a dielectric-loaded surface plasmon-polariton waveguide (DLSPPW).

Figure 4:
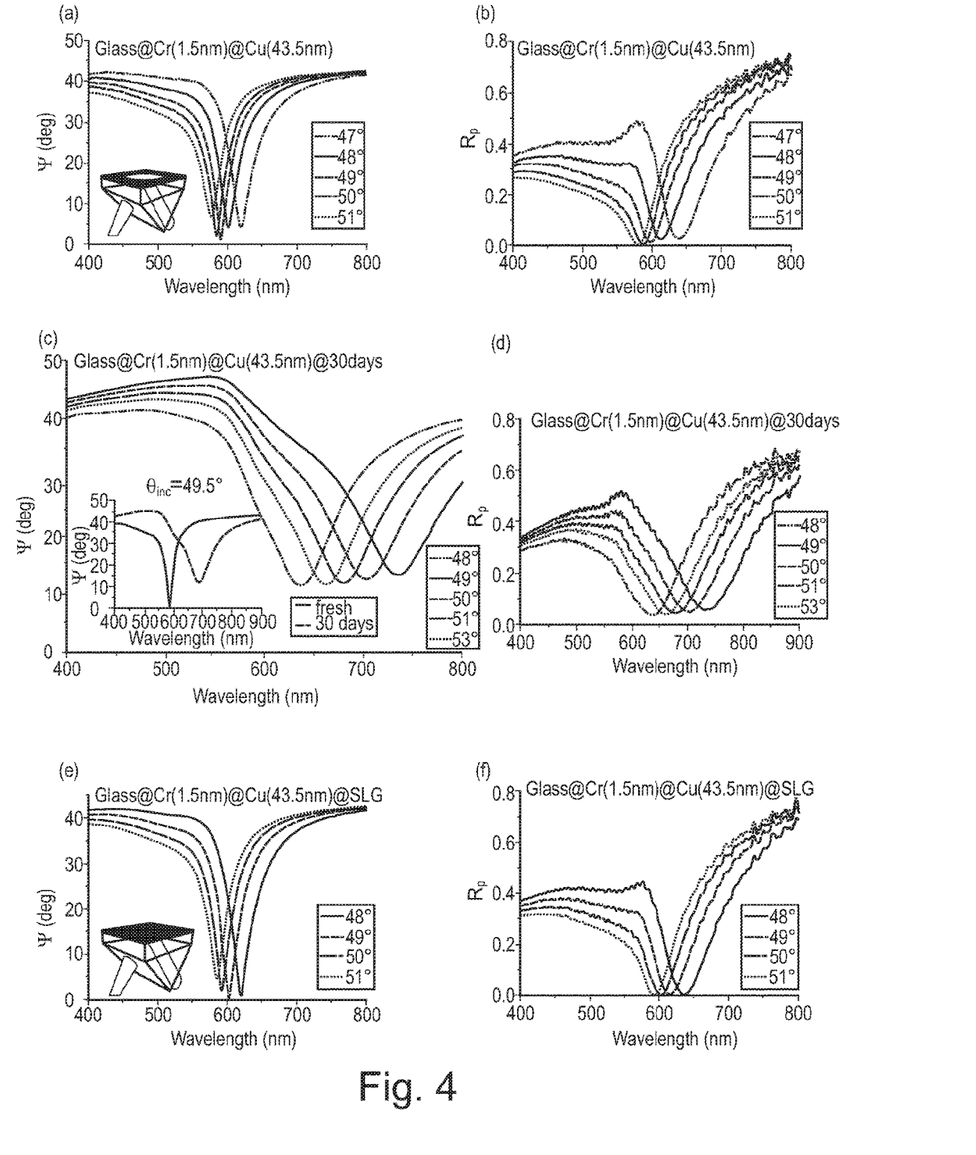
FIG. 4(a) shows the SPR ellipsometric reflection $\Psi$ for a fresh unprotected sample of copper (43.5 nm thick) as a function of wavelength ($\tan(\Psi)\exp(i\Delta)=r_p/r_s$, where $r_p$ and $r_s$ are reflection coefficients for p- and s-polarizations, respectively)
FIG. 4(b) shows p-polarized intensity reflection $R_p$ for the same sample as that of FIG. 4(a) as a function of wavelength.
FIGS. 4(c) and 4(d) show the same measurements as shown in FIGS. 4(a) and 4(b), respectively, after a period of 30 days, where the inset in FIG. 4(c) emphasises the degradation of the SPR in time.
FIGS. 4(e) and 4(f) show the same measurements as shown in FIGS. 4(a) and 4(b) for graphene-protected copper after a time period of half a year.

To assess the plasmonic properties of graphene-protected copper, surface plasmon resonance (SPR) was studied by using the Turbadar-Kretschmann-Raether geometry shown in FIG. 2 and the propagation of plasmon-polaritons was studied using the DLSPPW geometry shown in FIG. 3. The SPR for two Cu films (as fabricated; unprotected) are shown in FIGS. 4(a) and 4(b). For the Cu film of thickness d=43.5 nm the strongest resonance is observed at the angle $\theta_R$=49.5° for the wavelength $\lambda_R$=588 nm; the prism refractive index n was 1.5. The minimum reflection for the SPR curve is $\Psi_{min}$=0.7° (for the ellipsometric parameter) which translates into the minimum intensity reflection $R_{min}$=5×10$^{-4}$ (FIG. 4(b)). Here, tan($\Psi$) exp(i$\Delta$)=$r_p$/$r_s$, where $r_p$ and $r_s$ are reflection coefficients for p- and s-polarizations, respectively. The quality factors are Q=19 and 12, if extracted from the ellipsometric and reflection curves, respectively. Here $Q=\lambda_R/(\Delta\lambda_{FWHM})$ where $\lambda_R$ is the resonance wavelength corresponding to the SPR minimum and $\Delta\lambda_{FWHM}$ is the full-width of the resonance at half-minimum of the resonance curve. These characteristics are better than those observed for gold films with the SPR at the same wavelength, which can be attributed to the higher conductivity of copper and better morphology of films in accordance with the present invention.

Figure 5:
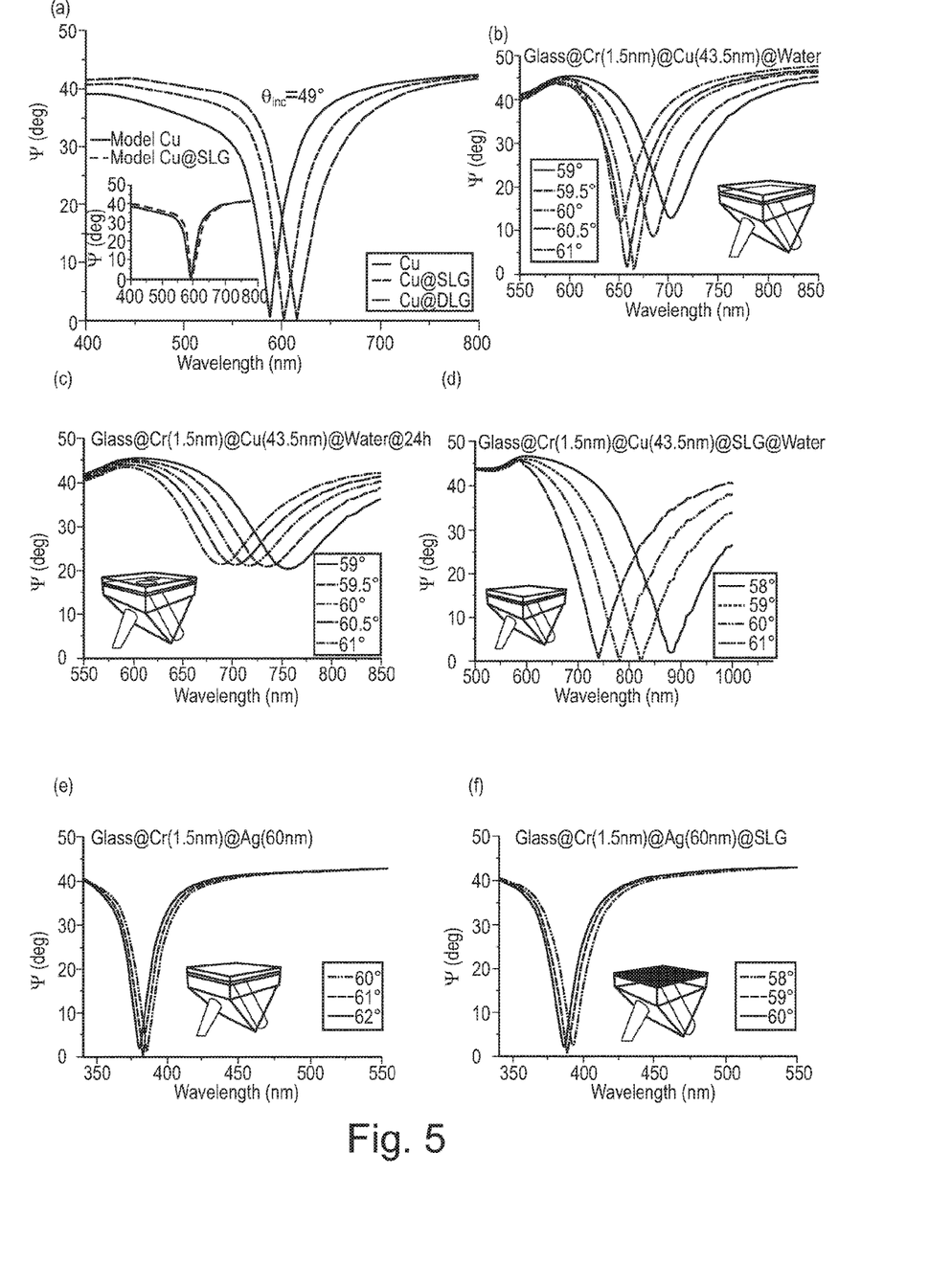
FIG. 5(a) shows the spectral dependence of the SPR measured at 49° in air for freshly fabricated unprotected copper, copper protected with a single graphene layer (SLG) and copper with a double layer protection (DLG), where d=43.5 nm, and the inset shows results of modelling for the same experiment.
FIG. 5(b) shows the SPR ellipsometric reflection $\Psi$ for a fresh unprotected copper sample in contact with water.
FIG. 5(c) shows the SPR ellipsometric reflection $\Psi$ for a fresh unprotected copper sample in contact with water after a period of 24 hours in water.
FIG. 5(d) shows the SPR ellipsometric reflection $\Psi$ for a graphene-protected copper sample in contact with water after half a year.
FIG. 5(e) shows the SPR ellipsometric reflection $\Psi$ for a fresh unprotected silver film, where d=60 nm.
FIG. 5(f) shows the SPR ellipsometric reflection $\Psi$ for a silver film covered with graphene, where d=60 nm.

If left exposed to air or even placed in a desiccator or low vacuum, the unprotected Cu samples oxidize rapidly and the quality of SPR deteriorates, as demonstrated in the results shown in FIGS. 4(c) and (d). After 30 days, the deepest SPR curve shifted to $\theta_R$=53° and the resonance minimum was observed at $\lambda_R$=637 nm. The minimum reflection increased by a factor of 20 to $\Psi_{min}$=11.5° and the minimum intensity by a hundred times to $R_{min}$4×10$^{-2}$, whereas the quality factor of the SPR curve dropped to Q=7 and 6 for the ellipsometric and reflection curves, respectively. In contrast, the samples protected by graphene did not show any degradation of plasmonic characteristics in the SPR curve even after one year. Moreover, graphene coating even improves the SPR quality, if graphene is transferred within minutes after exposing Cu films to air. In this case, FIGS. 4(e) and (f) show that for the graphene-covered part of the same Cu film with d=43.5 nm, the deepest SPR occurs at $\theta_R$=49° and $\lambda_R$=603 nm and exhibits $\Psi_{min}$=0.4° and $R_{min}$=3×10$^{-4}$. Q also increases to 20 and 13 for the ellipsometric and reflection curves, respectively. Such small values of $R_{min}$ could not previously be achieved for Au films, because of their morphology that has proven difficult to improve and control. At the same time, the reflectance $R_{min}$ is important for phase sensitive biosensing. For completeness, FIG. 5(a) provides a comparison of SPR curves measured in air for a fresh copper film, a film protected by one graphene layer (SLG=single layer of graphene) and a film protected by two graphene layers (DLG=double layer of graphene). It is found that each graphene layer induces a small red shift of ~10 nm in the SPR position. The inclusion of additional layers of graphene may minimize the risk of corrosion of the underlying metal due to occasional defects and cracks. In particular, by including more than one protective layer of graphene, the probability of defects in individual layers coinciding with one another is particularly low. Nevertheless, in many applications, a single layer of graphene is found to sufficiently preserve plasmonic properties over a long period of time (~1 year).

Main applications of the SPR lie in biosensing which necessitates a wet environment. The present invention is therefore particularly suitable for biosensing applications since the graphene is able to protect Cu films in water. FIG. 5(b) shows a SPR curve for an unprotected film measured in water immediately after evaporation. The SPR is observed at $\theta_R$=60° and $\lambda_R$=664 nm (n=1.8 in this case). The unprotected copper corrodes quicker in water than air, and the SPR notably degrades in just 24 hours, as shown in FIG. 5(c). It can be seen that $\Psi_{min}$ increases from 1° to 21° and Q drops from 19 to 9.5. On the contrary, graphene-protected films made in accordance with the present invention did not show deterioration in plasmonic properties in water over the whole period they were studied. FIG. 5(d) shows the typical SPR curves measured in water for a Cu film protected by a single layer of graphene. In water, graphene yields a red-shift of 115 nm (which is connected with the usage of SPR resonance of longer wavelengths that becomes more pronounced after graphene transfer) with a simultaneous decrease in Q. At the same time, the minimum reflection in the SPR curve drops to $\Psi_{min}$=0.3°.

The principles outlined above in relation to copper may be applied to any layer of metal in which the metal is selected from: a Group 8 to Group 11 transition metal, aluminium, germanium, antimony, or bismuth. For example, silver is well known as one of the best possible plasmonic materials but it is also notoriously known for its fast oxidation and degradation. Prior art attempts to use graphene coated silver for use in a plasmonic device were unsuccessful due to poor SPR response of such structures. The present invention permits barrier-layer protected silver-based plasmonic devices where the plasmonic properties of the silver are not detrimentally affected.

FIGS. 5(e) and (f) show SPR curves for a fresh silver film and a silver film covered with a monolayer of CVD graphene, respectively. It can be seen that graphene does not deteriorate the excellent SPR response of silver: the resonance minimum changes from $\Psi_{min}$=0.3° for the freshly prepared silver film (FIG. 5(e)) to $\Psi_{min}$=0.7° for graphene-protected Ag film (FIG. 5(f)).

The sensitivity of plasmonic structures in accordance with the present invention to binding chemicals is demonstrated experimentally below using reversible graphene hydrogenation.

In order to bind hydrogen to the graphene surface, a cold hydrogen dc plasma was used at a low-pressure (~0.1 mbar) $H_2$/Ar (1:10) mixture. The plasma was ignited between Al electrodes. The level of hydrogenation was estimated by measuring the D to G Raman peak intensity for hydrogenated samples registered by using a Renishaw RM1000 spectrometer at a 514 nm excitation wavelength. A typical distance between hydrogen sites $L_D$ was calculated as $L_D$=4.24×10$^{-5}\lambda^2\sqrt{I(G)/I(D)}$, where $\lambda$ is the wavelength measured in nanometers, I(G) and I(D) are the intensities for the G and D Raman peaks of hydrogenated graphene. This yields $L_D$≈10 nm after the 30 minutes of hydrogenation. It is assumed that the size of possible hydrogen clusters is smaller than the inter-cluster distance (~5 nm), which gives an estimate of 17% hydrogenation after 30 minutes. It should be noted that graphene hydrogenation is a reversible process which can be reverted by a soft anneal.

Figure 6:
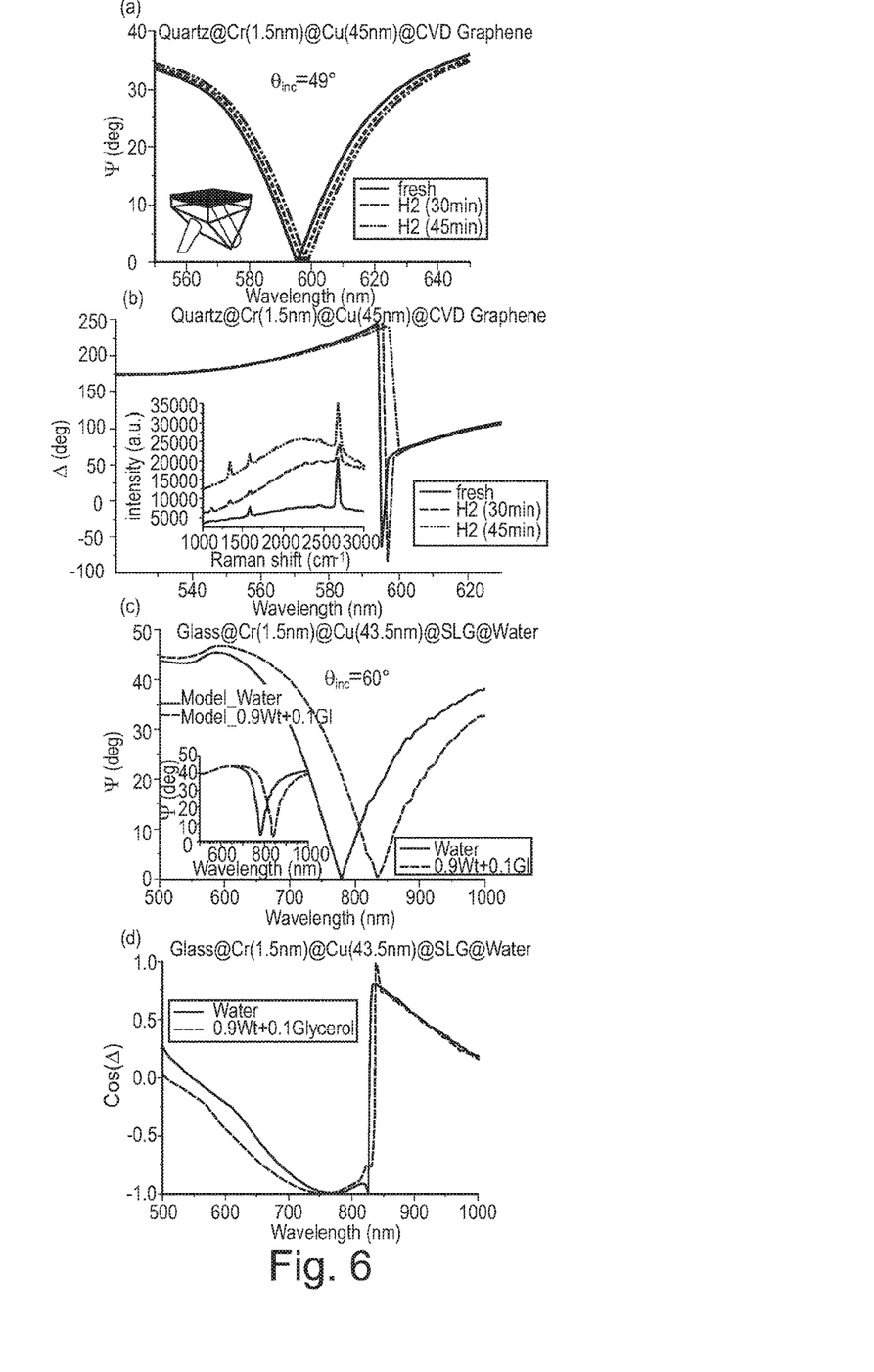
FIG. 6(a) shows SPR curves for various levels of graphene hydrogenation.
FIG. 6(b) shows the spectral dependence of the ellipsometric phase $\Delta$ for different hydrogenation levels, where the inset shows the corresponding Raman spectra.
FIG. 6(c) shows SPR curves for graphene protected copper in two different liquids, where coupling prism has refractive index n=1.8, with the inset showing the results of the modelling for the same experiment.
FIG. 6(d) shows the spectral dependence of the phase for the two liquids used for the experiment of FIG. 6(c)

Sensitivity to local environment (local refractive index) was also studied by utilizing glycerol-water mixtures. FIGS. 6(a) and 6(b) show evolution of ellipsometric parameters when samples were exposed to atomic hydrogen, which led to partial hydrogenation of the graphene layer. The hydrogenation ratio was monitored by Raman spectroscopy (inset of FIG. 6(b)) through the ratio of the intensity of the G and D peaks. The hydrogenation level after 30 minutes of the exposure was ≈17% which corresponds to the areal mass density σ of adsorbed hydrogen of ~10 pg/mm$^2$. Accordingly, the mass sensitivity of the graphene-protected SPR sensor in accordance with the present invention was $\delta\lambda/\sigma$~0.15 nm and $\delta\Delta/\sigma$~30° per pg/mm$^2$ in terms of wavelength and phase measurements, respectively. Assuming a minimal detectable phase shift of 5×10$^{-3}$ degrees, the minimal detectable adsorbed mass of ~0.2 fg/mm$^2$ is obtained. This detection limit is similar to that of plasmonic metamaterials with topological darkness and is four orders of magnitude better than the sensitivity achieved for gold-based plasmonics.

FIGS. 6(c) and (d) illustrate the sensitivity of SPR sensors in accordance with the present invention for bio-applications where changes in local environment were mimicked by replacing water (n=1.33) with a water-glycerol mixture (n=1.34). This change results in a pronounced red-shift of the SPR, which translates into the wavelength sensitivity $\delta\lambda/\delta n$~5600 nm/RIU, where RIU is the refractive index unit, and $\delta\Delta/\delta n$>2×10$^4$ deg/RIU for the phase measurements. The former sensitivity is comparable with the theoretically envisaged sensitivity for gold-based SPR sensors (~104 nm/RIU), whereas the latter is significantly better due to smaller reflection in the SPR minimum. It is worth mentioning that graphene and graphene oxide show good biocompatibility.

Barrier layer-protected metals in accordance with the present invention can also be used in complex plasmonic devices that require nanofabrications (for example, in waveguides and resonators). To this end, FIGS. 7(a) and 7(b) respectively show schematics and an optical micrograph of plasmon-polariton waveguide structures that were chosen as a test structure. The waveguides each consist of a DLSPPW made on top of graphene-protected copper and the coupling and de-coupling gratings.

The dielectric waveguide used as the test structures were produced by photolithography on graphene-covered Cu films by using the negative tone photoresist ma-N 1405 from Micro-resist Technology. The substrate was pre-heated to 200° C. in order to improve adhesion of the resist. A 250-nm thick resist layer spin-coated on to the sample was used and was patterned with the Microtech Laserwriter LW405 system. The pattern was developed in ma-D 533/S developer and rinsed in deionised water. Arrays of waveguides of width 1.0 μm and lengths 10 μm, 20 μm and 30 μm were fabricated. The pitch of coupling and de-coupling gratings was 1.2 μm; the grating ridge width was 1.0 μm.

To study light propagation in the waveguides, the waveguide coupler was illuminated with a 632.8 nm He—Ne laser at normal incidence by using a 100× objective lens to give a spot size of ~500 nm. The incident laser power was ~0.5 mW. The transmitted light intensity was evaluated from calibrated CCD images.

Figure 7:
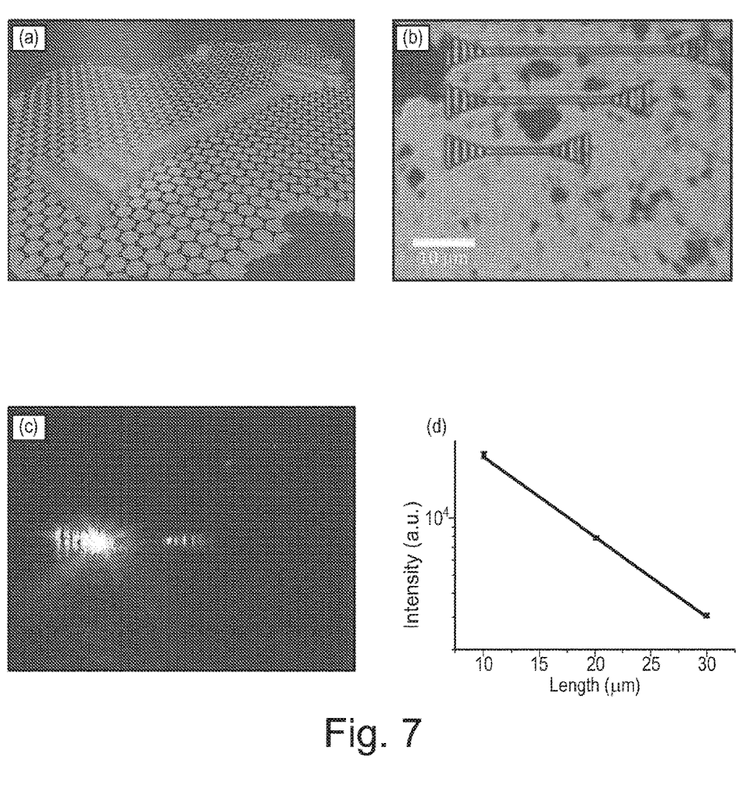
FIG. 7(a) shows schematics of a dielectric-loaded surface plasmon-polariton waveguide (DLSPPW)
FIG. 7(b) shows a microscopy image of fabricated DLSPPW waveguides.
FIG. 7(c) shows a CCD image of the light propagation along one of the waveguides of FIG. 7(b)
FIG. 7(d) shows the dependence of the transmitted light intensity on the length of one of the waveguides of FIG. 7(b)

FIG. 7(c) shows the observed radiation coming out from the decoupling grating. FIG. 7(d) shows the dependence of the transmitted light intensity as a function of the waveguide length. This yields the decay length for propagating waveguide modes of 10 μm, which suggests a strong contribution from photonic modes. This study demonstrates that radiation transfer between the in- and out-coupling gratings is well established. It is important to mention that Cu films without graphene protection would not survive the nanofabrication procedures that take time and involve baking steps speeding up Cu corrosion.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A plasmonic structure comprising:
   a layer of metal in which the metal is selected from: a Group 8 to Group 11 transition metal, aluminium, germanium, antimony or bismuth; and
   a barrier layer formed from less than 20 atomic layers of a 2-D material disposed on a surface of the layer of metal;
   wherein the metal layer has a roughness that permits the propagation of running plasmons along the interface of the metal layer and the barrier layer.

2. The plasmonic structure of claim 1, wherein the root mean square of the roughness of the surface of the layer of metal is less than 50 nm, and preferably less than 20 nm.

3. The plasmonic structure of claim 1, wherein the layer of metal is selected from: copper, silver, or aluminium.

4. The plasmonic structure of claim 1, wherein the layer of metal is selected from: iron, cobalt, nickel, ruthenium, rhodium, palladium, silver, osmium, iridium, platinum, gold, aluminium, germanium, antimony, or bismuth.

5. The plasmonic structure of claim 1, where the barrier layer includes one or more of: graphene, reduced graphene oxide, BN, $MoS_2$, $MoSe_2$, $MoTe_2$, $WS_2$, $WSe_2$, $WTe_2$, $TaS_2$, $NbSe_2$, $NbS_2$, $ReS_2$, $ReSe_2$, $TiS_2$, $TiSe_2$, black phosphorous, graphene, or fluorinated graphene.

6. The plasmonic structure of claim 1, wherein the layer of metal is a film, or wherein the layer of metal is an electron-beam evaporation grown layer or a sputtered layer.

7. The plasmonic structure of claim 1, wherein the barrier layer is a chemical vapour deposition (CVD) grown layer.

8. The plasmonic structure of claim 1, wherein the barrier layer includes graphene that is mechanically exfoliated prior to transfer onto the surface of the layer of metal.

9. A plasmonic device including the plasmonic structure of claim 1.

10. The plasmonic device of claim 9, wherein the device is a surface plasmon resonance (SPR) device configured to measure the SPR response of the plasmonic structure.

11. The plasmonic device of claim 10, wherein the plasmonic structure is mounted on a prism in a Turbadar-Kretschmann-Raether configuration.

12. The plasmonic device of claim 9, further comprising a dielectric-loaded surface plasmon-polariton waveguide (DLSPPW), wherein the plasmonic structure forms part of the DLSPPW.

13. The plasmonic device of claim 9, further including a complementary metal-oxide semiconductor (CMOS).

14. The plasmonic device of claim 9, wherein the plasmonic device is a biosensor for measuring one or more properties of an analyte.

15. The plasmonic structure of claim 1, wherein the metal layer has a roughness that permits the propagation of running plasmons along the interface of the metal layer and the barrier layer, such that $L/\lambda_0 \gg 1$, where L is the mean free path of plasmons due to roughness and $\lambda_0$ is the wavelength of incident light.

* * * * *